US00PP22790P2

(12) United States Plant Patent
Bryant

(10) Patent No.: US PP22,790 P2
(45) Date of Patent: Jun. 12, 2012

(54) ***AGLAONEMA* PLANT NAMED 'BRYANT QUEEN'**

(50) Latin Name: *Aglaonema hybrida*
Varietal Denomination: Bryant Queen

(75) Inventor: Theo Bryant, Zolfo Springs, FL (US)

(73) Assignee: Bryant Ag-Co, LLC, Zolfo Springs, FL (US)

( * ) Notice: Subject to any disclaimer, the term of this patent is extended or adjusted under 35 U.S.C. 154(b) by 0 days.

(21) Appl. No.: 13/134,168

(22) Filed: May 31, 2011

(51) Int. Cl.
*A01H 5/00* (2006.01)

(52) U.S. Cl. ..... Plt./376

(58) Field of Classification Search ..... Plt./376
See application file for complete search history.

*Primary Examiner* — Annette Para
(74) *Attorney, Agent, or Firm* — C. A. Whealy

(57) ABSTRACT

A new and distinct cultivar of *Aglaonema* plant named 'Bryant Queen', characterized by its relatively compact and outwardly arching plant habit; freely clumping habit; dense and full growth habit; narrowly lanceolate leaves with contrasting dark green and silver-colored markings and dark green-colored margins; and relative cold temperature tolerance.

2 Drawing Sheets

Botanical designation: *Aglaonema hybrida.*
Cultivar denomination: 'BRYANT QUEEN'.

BACKGROUND OF THE INVENTION

The present invention relates to a new and distinct *Aglaonema* plant, botanically known as *Aglaonema hybrida* and hereinafter referred to by the name 'Bryant Queen'.

The new *Aglaonema* plant is a naturally-occurring whole plant mutation of *Aglaonema hybrida* 'Silver Queen', not patented. The new *Aglaonema* plant was discovered and selected by the Inventor as a single plant from within a population of plants of 'Silver Queen' in a polypropylene-covered shadehouse in Zolfo Springs, Fla. on May 1, 2008.

Asexual reproduction of the new *Aglaonema* plant by cuttings in a controlled environment in Zolfo Springs, Fla. since May 2, 2008 has shown that the unique features of this new *Aglaonema* plant are stable and reproduced true to type in successive generations of asexual reproduction.

SUMMARY OF THE INVENTION

Plants of the new *Aglaonema* have not been observed under all possible environmental conditions and cultural practices. The phenotype may vary somewhat with variations in environment conditions such as temperature and light intensity, without, however, any variance in genotype.

The following traits have been repeatedly observed and are determined to be the unique characteristics of 'Bryant Queen'. These characteristics in combination distinguish 'Bryant Queen' as a new and distinct *Aglaonema* plant:

1. Relatively compact and outwardly arching plant habit.
2. Freely clumping habit.
3. Dense and full growth habit.
4. Narrowly lanceolate leaves with contrasting dark green and silver-colored markings and dark green-colored margins.
5. Relatively cold temperature tolerant.

Plants of the new *Aglaonema* differ from plants of the parent, 'Silver Queen', primarily in cold temperature tolerance as plants of the new *Aglaonema* are more cold tolerant than plants of 'Silver Queen'.

Plants of the new *Aglaonema* can be compared to plants of the *Aglaonema hybrida* 'Moonlight Bay', not patented. In side-by-side comparisons conducted in Zolfo Springs, Fla., plants of the new *Aglaonema* differed from plants of 'Moonlight Bay' in the following characteristics:

1. Plants of the new *Aglaonema* had smaller leaves than plants of 'Moonlight Bay'.
2. Plants of the new *Aglaonema* and 'Moonlight Bay' differed in leaf coloration as plants of 'Moonlight Bay' had duller and less contrasting coloration.
3. Plants of the new *Aglaonema* and 'Moonlight Bay' differed in petiole coloration as plants of 'Moonlight Bay' had solid green-colored petioles.

Plants of the new *Aglaonema* can also be compared to plants of the *Aglaonema hybrida* 'Emerald Bay', disclosed in U.S. Plant Pat. No. 12,867. In side-by-side comparisons conducted in Zolfo Springs, Fla., plants of the new *Aglaonema* differed from plants of 'Emerald Bay' in the following characteristics:

1. Plants of the new *Aglaonema* had smaller leaves than plants of 'Emerald Bay'.
2. Plants of the new *Aglaonema* and 'Emerald Bay' differed in leaf coloration as plants of 'Emerald Bay' had duller and less contrasting coloration and a wider dark green-colored margins.
3. Plants of the new *Aglaonema* and 'Emerald Bay' differed in petiole coloration as plants of 'Emerald Bay' had solid green-colored petioles.

BRIEF DESCRIPTION OF THE PHOTOGRAPHS

The accompanying photographs illustrate the overall appearance of the new *Aglaonema* plant showing the colors as true as it is reasonably possible to obtain in colored reproductions of this type. Colors in the photographs may differ slightly from the color values cited in the detailed botanical description which accurately describe the colors of the new *Aglaonema* plant.

The photograph on the first sheet is a side perspective view of a typical plant of 'Bryant Queen' grown in a container.

The photograph on the second sheet is a close-up view of a typical plant of 'Bryant Queen'.

DETAILED BOTANICAL DESCRIPTION

The aforementioned photographs and following observations and measurements describe plants grown during the early spring in 20-cm containers in a polypropylene-covered shadehouse in Zolfo Springs, Fla. Plants were grown under conditions and practices which approximate those generally used in commercial *Aglaonema* shadehouse production. During the production of the plants, day temperatures ranged from 29° C. to 35° C., night temperatures ranged from 24° C. to 29° C. and light levels averaged 2,500 foot-candles. Plants were 15 months old when the photographs and the detailed description were taken. In the following description, color references are made to The Royal Horticultural Society Colour Chart, 2007 Edition, except where general terms of ordinary dictionary significance are used.

Botanical classification: *Aglaonema hybrida* 'Bryant Queen'.

Parentage: Naturally-occurring whole plant mutation of *Aglaonema hybrida* 'Silver Queen', not patented.

Propagation:

*Type*.—By cuttings.

*Time to initiate roots, summer*.—About four weeks at 29° C.

*Time to initiate roots, winter*.—About six weeks at 18° C.

*Time to produce a rooted young plant, summer*.—About eight weeks at 29° C.

*Time to produce a rooted young plant roots, winter*.—About twelve weeks at 18° C.

*Root description*.—Fleshy, medium in thickness; white in color.

*Rooting habit*.—Freely branching; moderately dense.

Plant description:

*Plant and growth habit*.—Relatively compact and outwardly arching plant habit; freely clumping habit; short internodes; full and dense habit; moderately vigorous growth habit; suitable for 20-cm containers; developing leaves initially upright, then arching outwardly with development.

*Plant height, from soil level to top of leaf plane*.—About 41 cm.

*Plant diameter or spread*.—About 68 cm.

*Stem description*.—Clumping habit: Plants of the new *Aglaonema* are freely clumping with numerous clumps developing per plant. Aspect: Mostly upright. Strength: Strong; somewhat flexible. Length, soil level to junction to two youngest leaves: About 1.5 cm. Diameter: About 1.5 cm. Internode length: About 7 mm. Color: Close to 144A. Cataphylls: Not observed.

Foliage description:

*Arrangement*.—Alternate/whorled; simple.

*Length*.—About 28.5 cm.

*Width*.—About 4.5 cm.

*Shape*.—Narrowly lanceolate.

*Apex*.—Acuminate.

*Base*.—Obtuse to attenuate.

*Margin*.—Entire; slightly undulate.

*Texture, upper and lower surfaces*.—Smooth, glabrous.

*Venation pattern*.—Pinnate.

*Color*.—Developing leaves, upper surface: Ground color, close to 184B; chevrons and random markings, close to 146A or 147A; margins, close to 146A or 147A. Developing leaves, lower surface: Close to between 144A and 146C. Fully expanded leaves, upper surface: Ground color, close to 194A to 194B; chevrons and random markings, close to 147A; margins, close to 147A; venation, similar to surface coloration. Fully expanded leaves, lower surface: Closest to 147B; venation, closest to 147B.

*Petiole*.—Aspect: Mostly erect, outwardly arching with development. Length: About 15.5 cm. Diameter, distal: About 4 mm. Diameter, proximal, flattened: About 1.4 cm. Strength: Strong; flexible. Color: Closest to 147A with lighter random flecks and spots, closest to 147C to 147D. Wing length: About 8.5 cm. Wing diameter, base: About 6 mm. Wing color, outer surface: Close to 147A with lighter random flecks and spots, closest to 147C to 147D. Wing color, inner surface: Close to 147B to 147C.

Inflorescence description: Inflorescence development has not been observed on plants of the new *Aglaonema*.

Disease/pest resistance: Plants of the new *Aglaonema* have not been observed to be resistant to pathogens or pests common to *Aglaonema*.

Temperature tolerance: Plants of the new *Aglaonema* have been observed to be relatively cold-tolerant compared to other commercially-produced *Aglaonema* plants. Plants of the new *Aglaonema* have been observed to tolerate temperatures ranging from about 8° C. to about 44° C.

It is claimed:

1. A new and distinct *Aglaonema* plant named 'Bryant Queen' as illustrated and described.

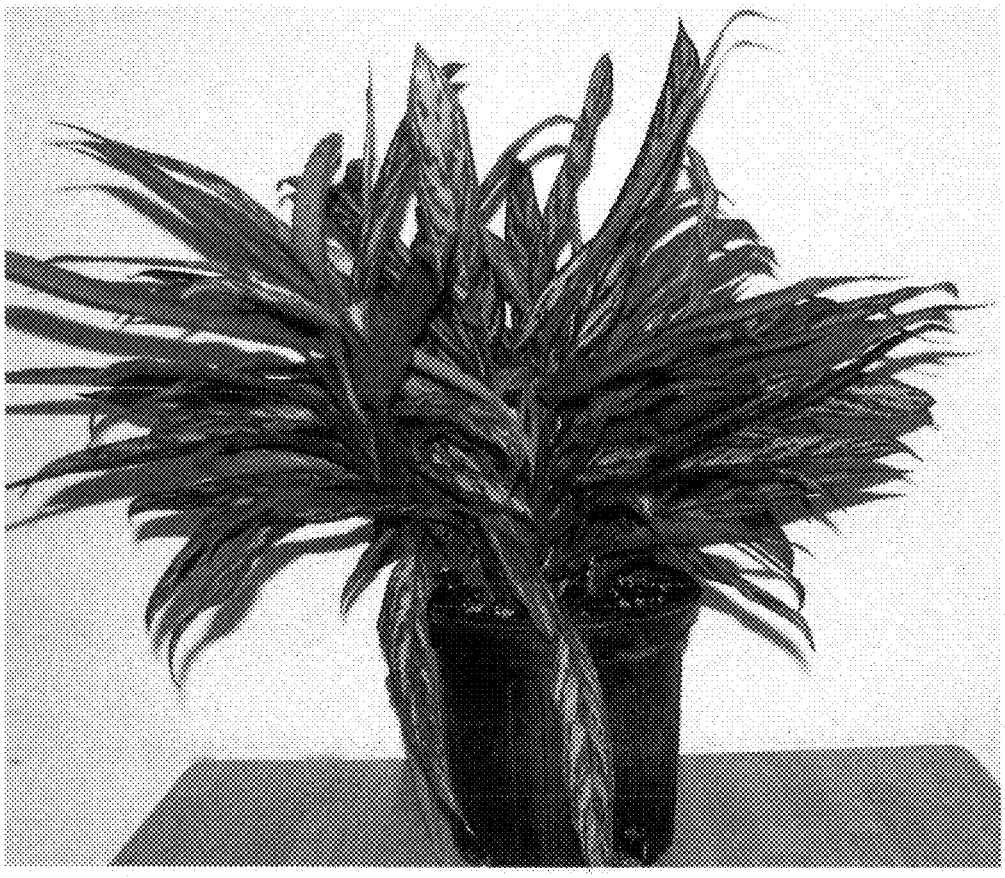

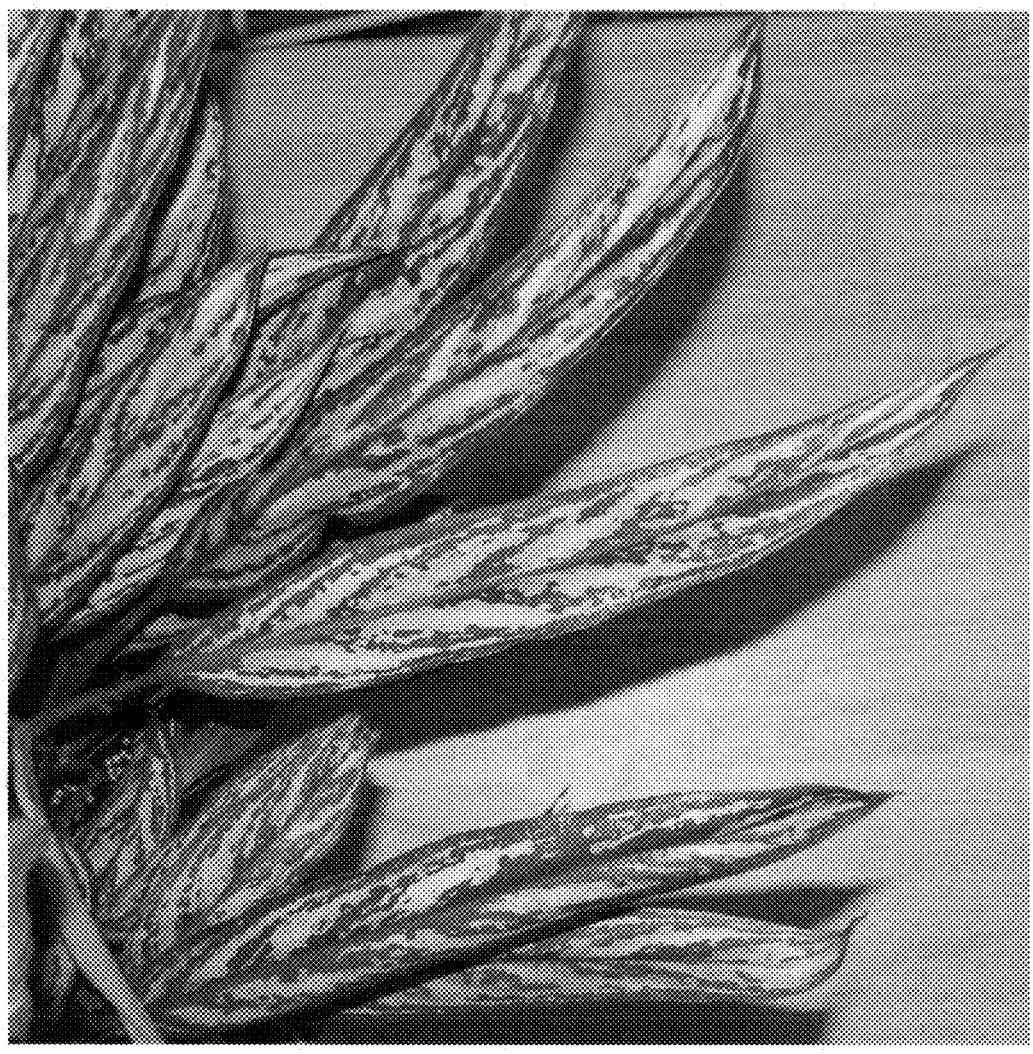

* * * * *